(12) United States Patent
Riebel et al.

(10) Patent No.: US 7,754,152 B2
(45) Date of Patent: Jul. 13, 2010

(54) ELECTRICAL CONNECTION SYSTEM FOR ELECTROCHEMICAL ANALYSIS SYSTEM

(75) Inventors: Stefan Riebel, Bellheim (DE); Bruno Robert Thoes, Quierschied (DE); Manfred Augstein, Mannheim (DE); Herbert Wieder, Mannheim (DE); Gregor Bainczyk, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1236 days.

(21) Appl. No.: 11/295,187

(22) Filed: Dec. 6, 2005

(65) Prior Publication Data

US 2006/0152207 A1  Jul. 13, 2006

(30) Foreign Application Priority Data

Dec. 15, 2004  (DE)  ........................ 10 2004 060 322
Oct. 10, 2005  (EP)  .................................. 05022049

(51) Int. Cl.
*G01N 27/00* (2006.01)
(52) U.S. Cl. ................. 422/82.02; 422/68.1; 422/82.01
(58) Field of Classification Search .................... 422/58, 422/64, 68.1, 82.02; 324/71.1
See application file for complete search history.

(56) References Cited

U.S. PATENT DOCUMENTS

| | | | |
|---|---|---|---|
| 3,980,376 | A | 9/1976 | Rosen |
| 4,654,197 | A | 3/1987 | Lilja et al. |
| 4,810,203 | A | 3/1989 | Komatsu |
| 5,108,564 | A | 4/1992 | Szuminsky et al. |
| 5,575,403 | A | 11/1996 | Charlton et al. |
| 5,609,823 | A | 3/1997 | Harttig et al. |
| 6,015,311 | A | 1/2000 | Benjamin et al. |
| 6,475,436 | B1 | 11/2002 | Schabbach et al. |
| 6,534,017 | B1 | 3/2003 | Bottwein et al. |
| 6,689,320 | B1 * | 2/2004 | Markart ...................... 422/68.1 |
| 2002/0057993 | A1 | 5/2002 | Maisey et al. |
| 2003/0203498 | A1 * | 10/2003 | Neel et al. ..................... 436/95 |
| 2004/0030353 | A1 | 2/2004 | Schmelzeisen-Redeker et al. |

FOREIGN PATENT DOCUMENTS

| | | |
|---|---|---|
| AU | 199921583 B2 | 6/1999 |
| DE | 43 26 339 A1 | 2/1995 |
| DE | 197 15 031 A1 | 10/1998 |
| DE | 198 54 316 A1 | 10/1999 |

(Continued)

*Primary Examiner*—Jill Warden
*Assistant Examiner*—Dean Kwak

(57) ABSTRACT

The invention relates to an electrical connection system for an analysis system and a method for analysis of a liquid sample on an analytical test element using the described analysis system. The analysis system comprises an evaluation appliance for evaluation of electrical signals, a test element holder for holding and positioning of an analytical test element in a measurement position, and at least one electrical contact element configured to make electrical contact with at least one electrical contact surface of an analytical test element, and to produce an electrical connection between the contact surface and the evaluation appliance. The at least one contact element is arranged to move to contact the contact surface of a test element held either in a fixed test element holder or a moveable test element holder, such as a slide. Furthermore, the analysis system has a means for moving the electrical contact element to the electrical contact surface of an analytical test element when the test element holder is in the measurement position.

5 Claims, 7 Drawing Sheets

FOREIGN PATENT DOCUMENTS

| | | |
|---|---|---|
| DE | 198 19 407 | 11/1999 |
| DE | 199 02 601 A1 | 7/2000 |
| EP | 0 738 666 B1 | 10/1996 |
| EP | 0 505 475 B1 | 3/1999 |
| EP | 1 321 769 A1 | 6/2003 |
| WO | WO 8502257 A1 * | 5/1985 |
| WO | WO 99/29429 | 6/1999 |
| WO | WO 01/89383 | 11/2001 |
| WO | WO 03/083469 | 10/2003 |

\* cited by examiner

ELECTRICAL CONNECTION SYSTEM FOR ELECTROCHEMICAL ANALYSIS SYSTEM

REFERENCE TO RELATED APPLICATIONS

The present application is based on German Patent Application No. DE 10 2004 060 322.7, filed Dec. 15, 2004 and European Patent Application No. EP 05022049.0, filed Oct. 10, 2005 which are hereby incorporated by reference in their entirety.

TECHNICAL FIELD

The present invention relates to an electrochemical analysis system and more particularly to an electrical connection system and method for electrically connecting a test element and an electrochemical evaluation appliance of the analysis system.

BACKGROUND

Analysis systems which allow individual parameters in sample liquids to be determined have been known for a long time, and many versions of them are commercially available. Particularly for the field of medical diagnosis and environmental analysis, appliances are offered which can also be operated by personnel with less training. Systems such as these which operate without the use of liquid reagents and in which, in general, no preparation of the sample material, or at least no complex preparation of the sample material, is required, are simple to operate. A "dry chemistry" has been developed for these so-called quick tests, in which the liquid contained in the sample liquid is used on its own as a solvent.

By way of example, systems for determination of glucose in the blood are in use, in which the patient places a small amount of blood on a test element, and carries out the measurement using an appliance which is simple to operate.

Conventional evaluation appliances have an opening, for example a slot, into which a test element can be inserted, typically by hand. Guide elements ensure that a test element is inserted in the intended orientation. The appliance typically has design features in order to ensure the desired positioning of the test element.

There are various forms of test elements. Those known include, for example, substantially small rectangular sheets, which are also referred to as strips, in whose center a multilayer test area is located. Diagnostic test elements which are in the form of strips are also referred to as test strips. Capillary test elements are known from the prior art, for example from WO 99/29429, for three-dimensional separation of a detection zone and a sample application point on a test element.

A large number of methods are known for measurement of the concentration of analytes, for example of glucose in a blood sample. Methods such as these are normally subdivided into one of two categories: optical methods or electrochemical methods.

Optical methods are based on color changes which produce an indication in the course of the verification reaction when the analytes to be determined are present. The color change which occurs on the test element can be detected by reflection-photometry. A transmission measurement is likewise possible, but in some cases necessitates the use of transparent test strips.

Electrochemical methods for determination of the concentration of an analyte are based, for example, on amperometry or coulometry. Methods such as these are known, for example, from the documents U.S. Pat. No. 4,654,197, EP 0 505 475 B1, US 2002/0057993 A1, EP 1 321 769 A1, WO 03/083469 A2 or U.S. Pat. No. 5,108,564. Electrical signals must be transmitted between the test element and the evaluation appliance in order to carry out the electrochemical analysis. A test element which has been introduced into an evaluation appliance therefore has to have electrical contact made with it in the evaluation appliance, with the aid of an electrical connection system.

Test elements which are used in the prior art are generally designed in layers and have contact surfaces in the form of thin metallic or otherwise conductive layers, in order to make electrical contact. In the case of evaluation appliances which are commercially available at the moment, the electrical contact elements of the appliance slide over the contact surfaces during the insertion of the test element, and can damage it in the process. Furthermore, material accumulations occur at the electrical contact elements of the evaluation appliance. Reliable contact can therefore not be ensured.

SUMMARY

One object of the present invention is thus to avoid the stated disadvantages of the prior art and to provide an analysis system having an electrical connection system for connecting an analytical test element to an evaluation appliance, and a method for electrical connection of a contact surface of a test element in an evaluation appliance, which allow reliable contact to be made between the test element and the evaluation appliance. A further aim is to avoid abrasive damage to the test element by the electrical contacts of the analysis system during insertion of the test element into a measurement position in the analysis system.

According to the invention, this object is achieved by an analysis system for analysis of a liquid sample on an analytical test element, comprising an evaluation appliance for evaluation of electrical signals, a test element holder configured to hold and position an analytical test element in a measurement position within the analysis system, and at least one electrical contact element configured to make electrical contact with at least one electrical contact surface of an analytical test element provided in the test element holder to produce an electrical connection between the contact surface and the evaluation appliance, wherein the at least one contact element is arranged such that it can move relative to the test element holder, and wherein the analysis system has a means for moving the electrical contact element into contact with the electrical contact surface of the analytical test element when the test element is positioned in the measurement position in the test element holder.

The object is also achieved by a method for analysis of a liquid sample on an analytical test element, including the steps of moving the analytical test element to a measurement position in a test element holder in an analysis system, and moving a contact element relative to the test element holder towards a contact surface of the test element in order to make electrical contact with the analytical test element and in order to produce an electrical connection between the contact surface and the evaluation appliance, and, using the evaluation appliance, evaluating an electrical signal which is transmitted from the test element via the contact surface and the contact element.

The analysis system according to the invention may, for example, be an appliance for evaluation of glucose in a body fluid, in particular in the blood. The liquid sample to be analyzed is passed to the test element which, if appropriate, contains reagents which react with components of the sample. For analysis purposes, this test element is moved manually or automatically to a measurement position in the test element holder in the evaluation appliance, before or after the sample is taken. The measurement position is in this case that position of the test element in the analysis system in which the electrochemical analysis of the sample on the test element takes place.

An electrical contact element makes contact with the test element when it is arranged in the measurement position for electrochemical analysis. For this purpose, the electrical contact element is moved towards a contact surface on the test element by the means for moving the electrical contact element, and contacts it, such as by pressing against it. At least when the test element is positioned in the measurement position, the contact element is in electrical communication with the evaluation appliance, for example with an electrochemical evaluation circuit configured to perform the analysis of the liquid sample based at least partially on the electrical signals transmitted from the test element. As a result, an electrical connection is produced between a test element in the measurement position and the evaluation appliance. Electrical signals are transmitted via this connection to the evaluation appliance, and are used to determine the glucose content or the content of some other electrochemically detectable analyte in the sample on the test element.

By making electrical contact with the test element using the analysis system according to the invention, and by using the method according to the invention, the contact element does not touch the contact surface of the analytical test element until the test element is positioned in the measurement position. The separation of the positioning of the test element and the process of making contact with it helps to prevent the contact element from grinding or scratching the contact surface. The electrode structure of the test element is thus not damaged this way. Since virtually no friction takes place between the at least one contact element and the at least one contact surface, very small contact surfaces can be used, thus resulting in a high miniaturization potential. The analysis system according to the invention and the method according to the invention also result in less risk of contamination to the contact element by the sample during removal of the test element with the sample from the measurement position after analysis, since the contact element is separated from the test element again, before removal. When contact is being made with the test element, the electrical contact element does not press against the contact surface with a high contact force until after positioning in the measurement position, thus ensuring a reliable contact and, if appropriate, additional fixing of the test element by means of the contact element.

According to one embodiment of the present invention, the contact element is moved at substantially right angles to the contact surface of an analytical test element which is held in the test element holder. This therefore avoids any parallel movement of the contact element with respect to the contact surface, and thus damage of the test element resulting from the contact element sliding over its surface. Furthermore, the contact element can be moved by a rotary movement towards the contact surface of an analytical test element which is held in the test element holder. The rotary movement is thus configured to result in substantially right angles as the contact element is in the vicinity of the contact surface.

A clamping device may be arranged in a test element holder of the evaluation appliance such that the clamping device fixes a test element, which is to be positioned in the measurement position, in the test element holder.

According to another embodiment of the present invention, a housing is provided for the analysis system generally or particularly for the evaluation appliance, with the test element holder and/or the means for moving the electrical contact element being arranged such that they or it can move relative to the housing. The contact element can be displaced by the means for moving the contact element either by the movement of the test element holder relative to the means for moving, or by movement of the means for moving relative to the housing (with the test element holder remaining fixed), so that the contact element is ultimately moved towards the test element as or after the test element is positioned in the measurement position. Electrical contact is thus made with the test element. The analysis system may also contain a drive for moving the test element holder and/or the means for moving the electrical contact element, or the test element holder and/or the means for moving the electrical contact element can be driven manually.

The analysis system according to the invention may also contain a test element magazine for holding at least two test elements, and a test element removal device for automatic removal of a test element from the test element magazine and for transport of the test element to the measurement position in the test element holder. Various test element magazines are known from the prior art, for example as disclosed in DE 198 19 407 and DE 198 54 316 A1, each of which are hereby incorporated by reference herein. Examples of test element removal devices are disclosed in EP 0 738 666 B1, DE 197 15 031 A1, U.S. Pat. No. 5,575,403, DE 199 02 601 A1, and DE 43 26 339 A1, which are also hereby incorporated by reference herein.

The invention also relates to an analysis system having an electrical connection system for connecting an analytical test element to an evaluation appliance, with the test element having at least one contact surface. The analysis system has a slide which can be moved between an initial position and an end position in a housing and contains a holding space with an inlet opening for holding the test element, with the holding space being bounded by a stop, and at least one contact element (possibly mounted on the slide), which is arranged such that, when the slide is in the initial position, it is at a distance from the contact surface of a test element which is held in the holding space, and such that it is moved from the initial position to the end position towards the contact surface by movement of the slide, and is pressed against the contact surface. The evaluation appliance according to the invention comprises an electrochemical evaluation circuit which is electrically connected to the contact element, at least in the end position of the slide. In this case, the slide is used as the test element holder. During movement of the slide, a means for moving the electrical contact element acts on the electrical contact element and moves it towards the contact surface.

In one embodiment, the test element is pushed into the test element holder through the inlet opening into the holding space in the slide for analysis of a liquid sample on a test element, with the slide being located in its initial position. When using a test element in the form of a strip, by way of example, the inlet opening is in the form of an elongated slot. The holding space is a cavity which is formed in the slide and into which the test element can be inserted until it reaches the stop. When the slide is in the initial position, a contact element which is mounted on it is at a distance from the contact surface of the test element. When the test element is pushed into the slide, the contact element does not touch the test element.

As soon as the test element has been inserted into the slide as far as the stop, the slide is moved away from the initial position to the end position, by means of the force which is still maintained in the insertion direction. The test element can be clamped in the holding space during the movement of the slide from the initial position to the end position, thus preventing any change in its position relative to the slide. By way of example, the end position of the slide may be defined by a further stop, which limits the movement of the slide. The movement of the slide from the initial position to the end position results in the contact element being moved towards the contact surface and being pressed against the contact surface, this resulting in electrical contact with the test element.

During the movement of the slide from its initial position to its end position, the test element does not move in the slide with respect to the slide and the contact element. It remains arranged in the same position in the holding space in the slide, resting on the stop. Electrical contact is thus made when the contact element, which is pressed against the test element, is moved with the slide, thereby avoiding the test element sliding over the contact element resulting in damage to the test element or accumulation of material on the contact element.

The sample which is located on the test element can be analyzed electrochemically in the end position, which thus comprises the measurement position. The electrochemical evaluation circuit is used for this purpose, and is electrically connected to the contact element, at least when the slide is in the end position. This electrical connection can be produced by the movement of the slide to the end position. However, the evaluation circuit can also be continuously electrically connected to the contact element.

The electrochemical evaluation circuit is used, for example, for evaluation of measured electrical signals which depend on the concentration of an analyte on the test element with which contact is made. Electrochemical evaluation circuits such as these are known from the prior art, for example from EP-B1 0505475 or from U.S. Pat. No. 5,108,564, which are hereby incorporated by reference herein.

In another embodiment of the present invention, the contact element is arranged recessed in a depression in the slide when the slide is in the initial position. The recessing of the contact element results in it being at a distance from the contact surface of the test element when the slide is in the initial position (in particular during insertion of the test element into the holding space).

A clamping device may be arranged in the holding space of the slide, such that it fixes a test element, which has been inserted into the slide as far as the stop, in the holding space.

The contact element in one embodiment extends through an opening in the slide, thereby reaching from the holding space within the slide to the outside of the slide. The contact element is then arranged such that it interacts with a contact-pressure element on the outside of the slide. In further embodiments, the contact-pressure element has a guide surface which is arranged such that it pushes the contact element into the holding space, towards the contact surface of a test element contained in it while the slide is being moved from its initial position to its end position. During the movement of the slide from the initial position to the end position, the guide surface of the contact-pressure element which is arranged outside the slide drives the contact element, which extends through the opening to the outside of the slide, such that it is pressed into the holding space within the slide until a contact is made with the contact surface of the test element. In one embodiment, the guide surface is inclined in the direction of insertion and can have a curved surface or comprise a substantially flat plane.

The electrical connections of the electrochemical evaluation circuit in the evaluation appliance can be connected directly to the contact element. However, they can also be connected to the contact-pressure element, which must then be electrically conductive, in order to achieve electrical contact with the contact surface of the test element upon interaction with the contact element.

In another embodiment of the present invention, the contact-pressure element is resiliently flexible and is resiliently deformed when the slide is in the end position, such that it presses the contact element against the contact surface of the test element with an additional force. Resilient deformation which is produced by the pressure put on the contact-pressure element, for example by the bending of the flexible contact-pressure element, results in the contact element being subjected to a force in the opposite direction to the deforming force, pressing the contact element against the contact surface of the test element.

In yet other embodiments, the contact element itself is resiliently flexible. The contact element is then deformed resiliently, such as by pressure applied by the contact-pressure element, such that it presses against the contact surface with a force (which if appropriate opposes the deforming force).

The invention also relates to an electrical connection system in an analysis system. The electrical connection system has a slide which can be moved between an initial position and an end position in a housing and contains a holding space with an inlet opening for holding a test element having at least one contact surface, with the holding space being bounded at least by a stop. The electrical connection system also has at least one contact element, which is arranged such that, when the slide is in the initial position, it is at a distance from the contact surface of a test element which is held in the holding space, and such that it is moved from the initial position to the end position towards the contact surface by movement of the slide, and is pressed against the contact surface.

The invention also relates to an analysis system for analysis of an analyte in a liquid sample, comprising an evaluation appliance which contains at least one electrical connection system according to the invention. The analysis system may also comprise a device for removal of body fluid from a body part. A large number of body fluid removal devices are known from the prior art, for example from WO 01/89383. These are used, for example, to obtain venous blood from the finger tips, or blood or interstitial fluid from other body parts. The body fluid obtained in this way is applied to the test element in order to be analyzed by the analysis system, for example for evaluating its glucose content.

In yet other embodiments, the analysis system may have a supply container for test elements and a removal apparatus for automatic removal of at least one test element from the supply container. The analysis system according to this embodiment is an integrated system, by means of which the taking of a sample (for example perforation of the skin and application of blood to a test element which has been taken from a supply container, has been transported to the sample taking position and has been positioned there) and sample analysis (for example transport and positioning of the test element with the sample in the measurement position, measurement and evaluation of the relevant variables, indication of the analysis result) are carried out automatically.

The invention also relates to an analysis system for analysis of a liquid sample on a test element, comprising a housing, an evaluation appliance for evaluation of electrical signals and at least one electrical contact element which is used to make electrical contact with at least one electrical contact surface of an analytical test element for enabling an electrical connection to the evaluation appliance. The evaluation appliance according to the invention also includes a test element holder which is arranged firmly relative to the housing of the analysis system. The test element holder thus cannot be moved relative to the housing. In the analysis system according to this embodiment, the at least one contact element is arranged such that it can move relative to the test element holder. The analysis system also has means for moving the electrical contact element to the electrical contact surface of an analytical test element when it is positioned in the measurement position in the test element holder.

Also in this embodiment, the means for moving the electrical contact element is moved manually or automatically (for example by means of an electric motor) in order to operate the electrical contact element so that it is moved to the contact surface of the test element.

According to another embodiment of the present invention, the analysis system has a test element magazine for at least two test elements, and a test element removal device for removal of test elements from the test element magazine, with the test element removal device having a drive by means of which the means for moving the electrical contact element can also be moved. For example, in the already described removal device from the prior art with a plunger, the plunger is driven via a coupling to a threaded rod which is rotated by an electric motor. In the analysis system according to the invention, the means for moving the contact element may, for example, likewise be moved via a coupling to this threaded rod by means of the electric motor of the removal device. In this case, the means for moving the electrical contact element can be a rod which can be moved substantially in the longitudinal direction and has a rod end by means of which the electrical contact element, which is in the form of an electrical toggle lever, can be moved to the contact surface of a test element which is positioned in the measurement position in the test element holder. The toggle lever is in this case preloaded by a spring element such that it is located in a position away from the test element holder until it is operated by the rod end. During test element removal from the test element magazine, the rod is moved parallel to the plunger, and the rod end reaches and operates the toggle lever only when the test element that has been removed has reached the measurement position in the test element holder. The rod end then tilts the toggle lever, which is provided as the contact element, so that it makes electrical contact with the test element, and makes an electrical connection to the evaluation appliance.

The statements which have been made above with reference to the electrical connection system according to the invention and the analysis system according to the invention apply (to the extent that they are applicable) in the same way to the method according to the invention.

The invention also relates to a method for electrical connection of a contact surface of a test element in an analysis system, having the following steps: inserting the test element into a holding space as far as a stop in a slide which is arranged in a housing such that it can be moved between an initial position and an end position, with the slide being located in the initial position, and a contact element connected to the slide being at a distance from the contact surface of the test element when the slide is in the initial position, and moving the slide with the test element contained in it from the initial position to the end position, with the contact element being moved towards the contact surface of the test element as a result of such moving, and being pressed against the contact surface when the slide is in the end position.

The invention also relates to a method for analysis of a liquid sample on an analytical test element, including the following steps: moving the analytical test element to a measurement position in a test element holder in an evaluation appliance, and moving a contact element relative to the test element holder towards a contact surface of the test element which is arranged in the measurement position, in order to make electrical contact with the analytical test element and in order to produce an electrical connection to the evaluation appliance, and using the evaluation appliance, evaluating an electrical signal which is transmitted from the test element via the contact surface and the contact element, by the evaluation appliance, wherein the analytical test element is moved to the measurement position in a test element holder which is arranged to be fixed relative to a housing of the evaluation appliance.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following description of embodiments of the invention, which are intended to illustrate the invention, but not limit the scope thereof.

DETAILED DESCRIPTION

The following description of the preferred embodiment is merely exemplary in nature and is in no way intended to limit the invention or its application or uses.

Figure 1:
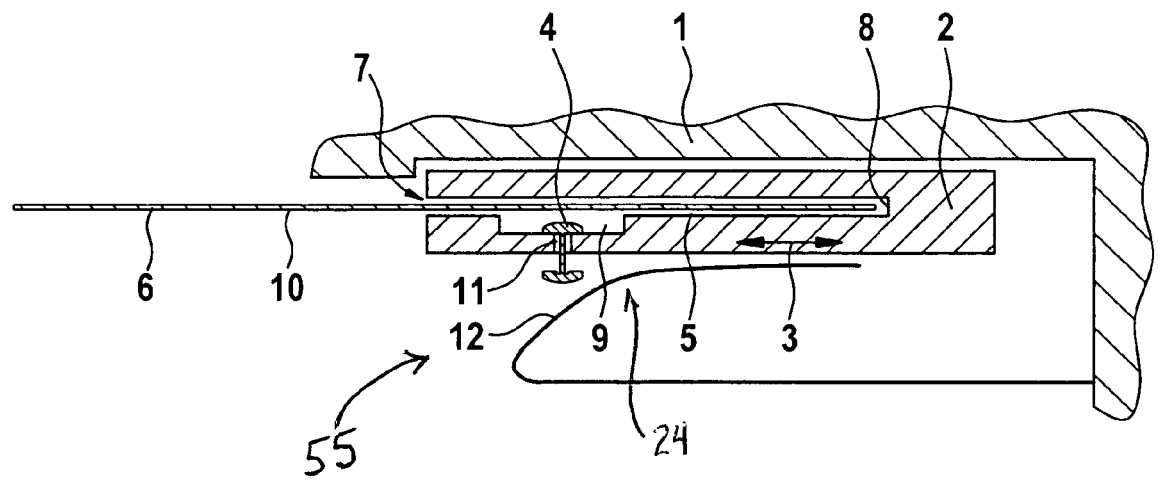
FIG. 1 shows a schematic illustration of one embodiment of an electrical connection system, which is contained in an analysis system according to the present invention, for a test element.

FIG. 1 shows one particular embodiment of an electrical connection system which is contained in an analysis system according to the present invention, for electrical connection of a test element 6 to an evaluation appliance 55.

Figure 5:
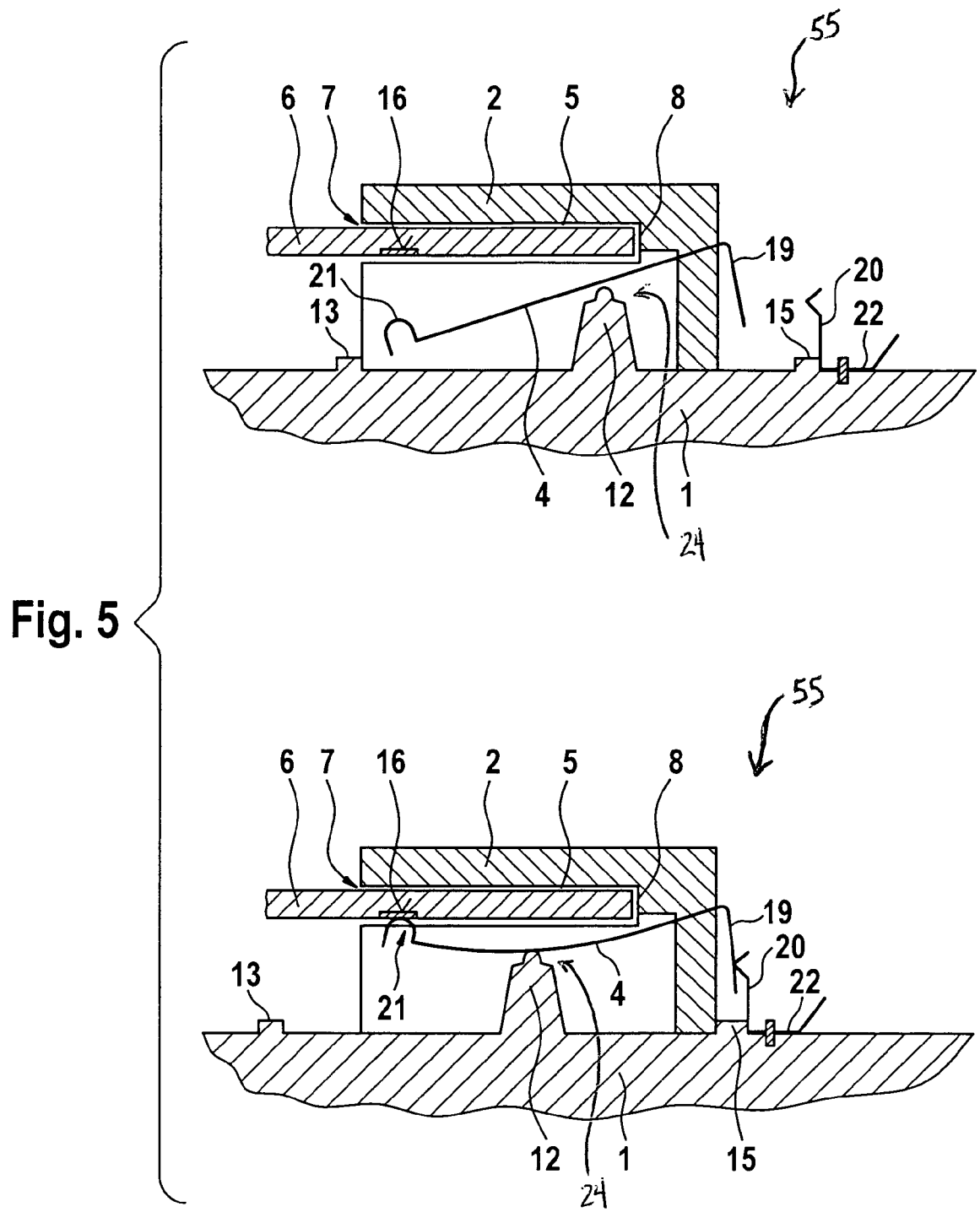
FIG. 5 shows a schematic illustration of a fourth embodiment of an electrical connection system for an analysis system according to the present invention, and the process of making contact with a test element contained in it.
Figure 6A:
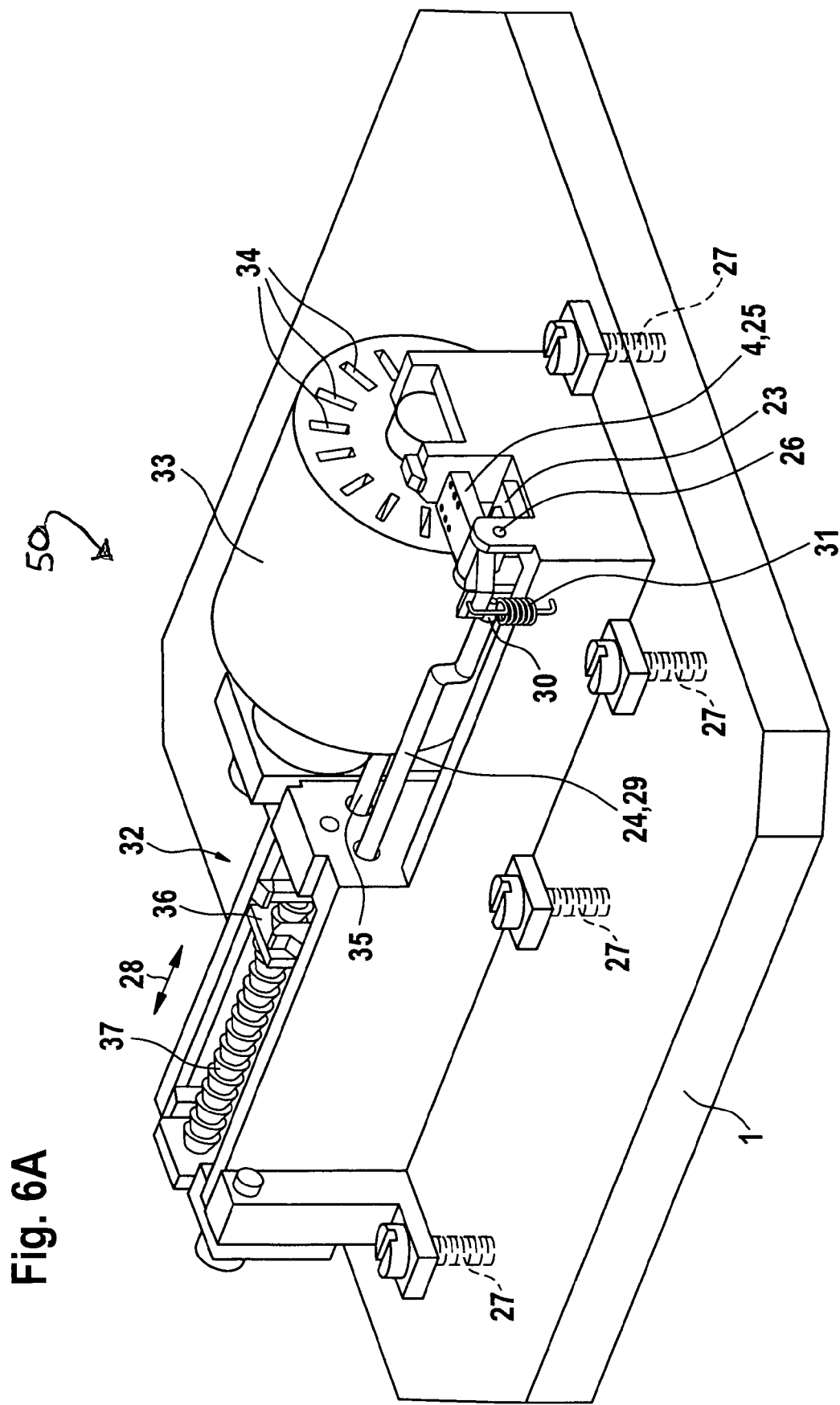
FIG. 6A shows a fifth embodiment of an analysis system according to the present invention.

A slide 2, such as a test element holder 23 (an example of which is shown in FIG. 6A), is arranged in a housing 1. The slide 2 can be moved in the housing 1, in the movement direction indicated by the double-headed arrow 3. An electrical contact element 4 is mounted on the slide 2 and is also moved in the movement direction 3 during movement of the slide 2. The slide 2 is illustrated in its initial position in FIG. 1. The slide 2 defines a holding space 5 for holding a test element 6. The holding space 5 extends in the slide 2 from the inlet opening 7 (which is exemplified in the form of a slot for purposes of receiving a strip-type test element) as far as a stop 8. The test element 6 is inserted into the holding space 5 as far as the stop 8 through the opening 7 with the slide 2 in the initial position. When the slide 2 is in the initial position, the contact element 4 is arranged recessed with respect to the test element 6, in a depression 9 in the holding space 5. In the initial position, the contact element 4 is thus at a distance from the test element 6, and does not touch it. The test element 6 has (on its lower face 10 in FIG. 1) at least one contact surface 16 (shown in FIGS. 3-5), which is arranged directly opposite the contact element 4 when the test element 6 has been inserted into the holding space 5 in the slide 2 as far as the stop 8.

The contact element 4 extends through and is moveably maintained within an opening 11 in the slide 2. A contact-pressure element 12 is provided on the outside of the slide 2, as the means 24 for moving the contact element, and interacts with the contact element 4, as will be explained in more detail in the following text with reference to FIGS. 2A to 2C.

Figure 2A:
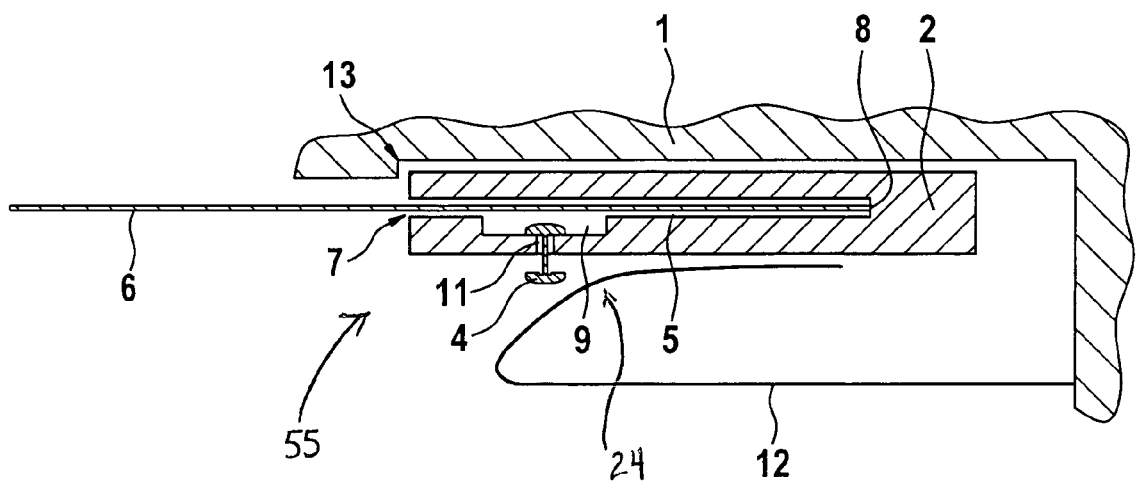
FIGS. 2A to 2C show three steps in the process of making contact with a test element in an electrical connection system as shown in FIG. 1.
Figure 2B:
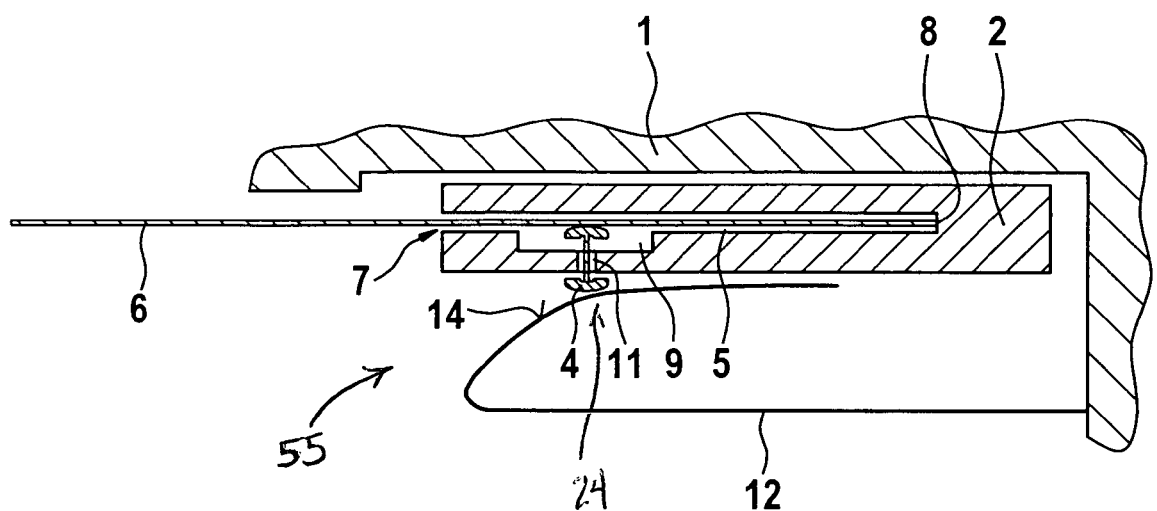
Figure 2C:
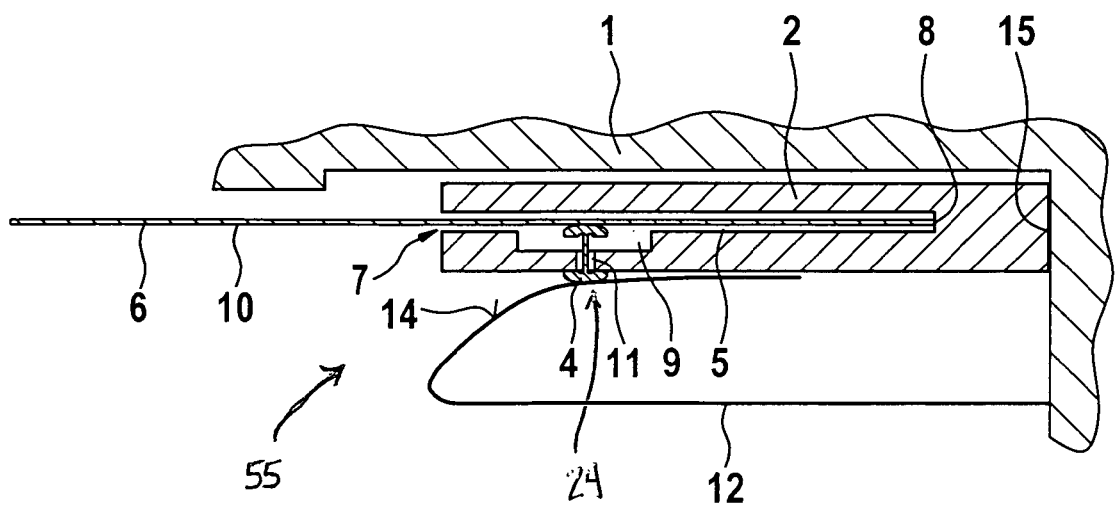

FIGS. 2A to 2C show three steps in the process of making contact with the at least one contact surface of a test element in the electrical connection system shown in FIG. 1.

FIG. 2A shows the slide 2 in the initial position in the housing 1. The slide 2 is in this case located against a first stop 13 in the housing 1. The contact element 4 is arranged recessed in the depression 9 in the holding space 5. A test element 6 is inserted into the holding space 5 through the inlet opening 7 until it meets the stop 8. During this process, the slide 2 remains in its initial position. The separated (recessed) arrangement of the contact element 4 in the holding space 5 prevents the test element 6 from sliding over the contact element 4 during insertion into the holding space 5, and prevents damage to the test element 6 or contamination of the contact element 4, as may occur during this process in conventional connection systems. Furthermore, the contact element 4 extends through and is moveably maintained within the opening 11 in the slide 2 to the outside, but is at a distance from the contact-pressure element 12.

FIG. 2B shows the slide 2 in a position in the housing 1, which is between the initial position and the end position. Once the test element 6 has been inserted, as is shown in FIG. 2A, as far as the stop 8 into the slide 2, the slide 2 is moved to its end position together with the test element 6 in the insertion direction by a continuous manually or automatically applied force. During this process, the contact element 4 interacts with the contact-pressure element 12 in such a way that, as soon as it reaches the contact-pressure element 12, it slides over a guide surface 14, which is in the form of a incline, on the contact-pressure element 12 and is resultingly displaced through the opening 11 into the holding space 5 to the contact surface of the test element 6. The contact element 4 is moved at substantially right angles to the contact surface during this process. In contrast, no relative movement of the contact element 4 parallel to the surface of the test element 6, which could result in damage to the surface, is produced, by virtue of the mounting of the contact element 4 in the slide 2.

During insertion of the slide 2, the test element 6 can be fixed by means of a clamping device (not illustrated) in the holding space 5 such that it rests on the stop 8, so that it does not move therein during insertion of the slide 2.

FIG. 2C shows the slide 2 in the end position in the housing 1. The end position is defined by a second stop 15 for the slide 2 in the housing 1, and represents the measurement position for the test element, which rests on the stop 8 in the holding space 5 in the slide 2. The contact element 4 is pressed against the contact surface on the lower face 10 of the test element 6, so that an electrical contact is produced. The contact-pressure element 12 is composed of a resiliently flexible material. It is thus bent downward by the contact element 4, which presses against the contact surface 16 of the test element 6, in the end position as illustrated in FIG. 2C, so that it exerts a corresponding opposing force on the contact element 4 upward (against the contact surface 16).

Once the analysis of the sample has been carried out with the aid of an electrochemical evaluation circuit (not illustrated), which is located in the evaluation appliance 55, the test element 6 is pulled in the direction of the initial position of the slide 2. In consequence, the slide 2 is moved together with the test element 6, which is fixed in it, as far as its first stop 13, and the test element 6 is then moved to its first stop 13, and the test element 6 is then pulled out of its holding space 5, with the contact element 4 once again being recessed with respect to the test element 6 in the depression 9, as in FIG. 2A. The electrical connection system is once again located in its initial position, ready for the next contact-making process.

Figure 3:
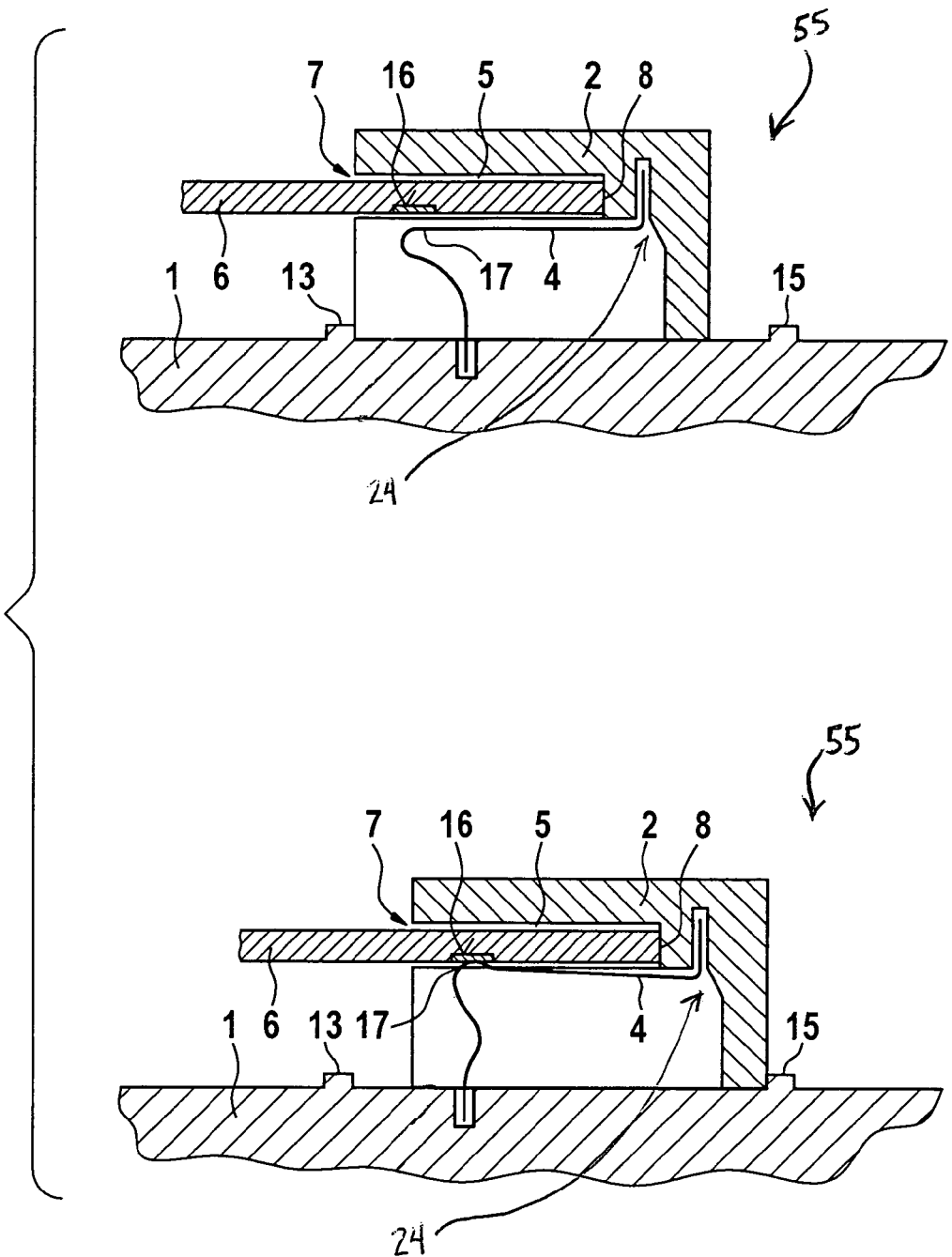
FIG. 3 shows a schematic illustration of a second embodiment of an electrical connection system for an analysis system according to the present invention, and the process of making contact with a test element contained in it.

FIG. 3 shows a schematic illustration of a second embodiment of an electrical connection system in an analysis system according to the present invention, for electrical connection of a test element 6 to an evaluation appliance 55.

The electrical connection system has a housing 1 in which a slide 2 (test element holder 23) can be moved between an initial position (FIG. 3, top) and an end position (FIG. 3, bottom). The slide 2 contains a holding space 5 with an inlet opening 7, in which a test element 6 is held in FIG. 3. The holding space 5 is bounded by a stop 8. The electrical connection system illustrated in FIG. 3 also has an electrical contact element 4, which is at a distance from the contact surface 16 of the test element 6 when the slide 2 is in the initial position (FIG. 3, top). In the initial position, the slide 2 rests on a first stop 13. The contact element 4 has a plurality of bends and is attached to the housing 1 at one end (and ultimately to an electrochemical evaluation circuit, now shown), and to the slide 2 at the other end. During manual or automatic movement of the slide 2 with a test element 6 contained in it from the initial position (FIG. 3, top) to the end position (FIG. 3, bottom), the contact element 4 is resiliently deformed. The resilient deformation is produced by that end of the contact element 4 which is attached to the slide 2 being moved together with the slide 2 relative to the housing 1, while the position of that end which is attached to the housing 1 does not change. As a result of the resilient deformation of the contact element 4, a sub area 17 of the contact element 4 which is arranged close to the contact surface 16 of the test element 6 is moved towards the contact surface 16 and is pressed against the contact surface 16 in the end position of the slide 2, thus producing an electrical contact in the measurement position. The slide 2 is thus itself used as the means 24 for moving the contact element 4. In the end position (FIG. 3, bottom), the slide 2 rests on a second stop 15. During movement of the slide 2 from the end position back to the initial position, the movement of the contact element 4 is reversed, and the electrical contact is disconnected again.

Figure 4:
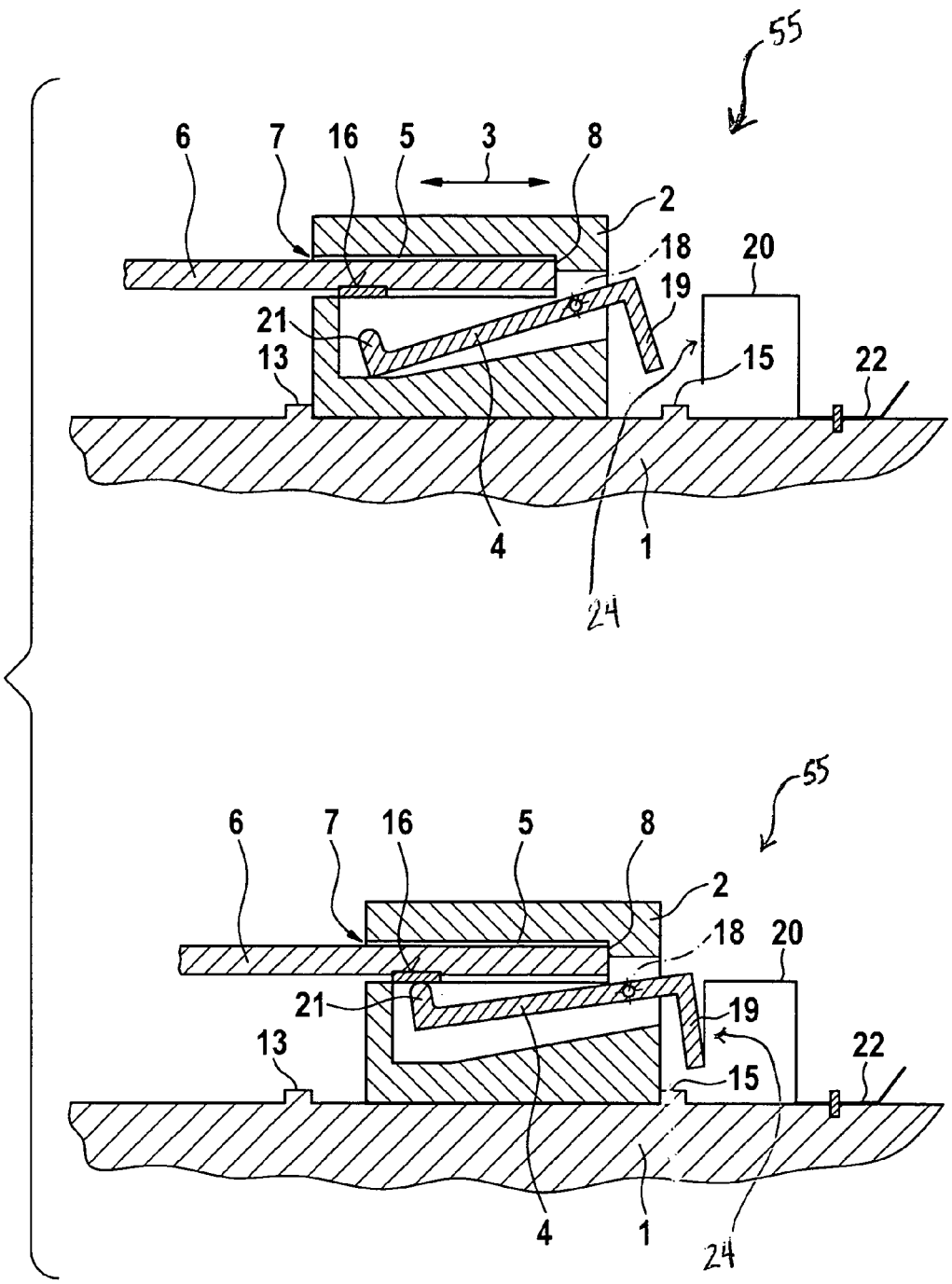
FIG. 4 shows a schematic illustration of a third embodiment of an electrical connection system for an analysis system according to the present invention, and the process of making contact with a test element contained in it.

FIG. 4 shows a third embodiment of an electrical connection system in an analysis system according to the invention, for electrical connection of a test element 6 to an evaluation appliance 55.

The electrical connection system comprises a housing 1 and a slide 2 that can be moved between an initial position (FIG. 4, top) and an end position (FIG. 4, bottom) (movement direction 3). During this process, the slide 2 is moved from a first stop 13 to a second stop 15. A test element 6 is arranged in a holding space 5 with an inlet opening 7 and a stop 8. An electrical contact element 4, which is mounted such that it can rotate about an axis 18, is mounted on the slide 2. The test element 6 has a contact surface 16. One end 19 of the contact element 4 strikes an electrical contact 20 when the slide 2 is in the end position. The electrical contact 20 is used as the means 24 for moving the contact element, and presses against the end 19 which is configured such that the contact element 4 is resultingly moved, by a rotary movement about the axis 18 which causes movement of its other end 21, towards the contact surface 16 of the test element 6, which is held in the measurement position in the slide, and makes electrical contact with it. The electrical contact then exists between the contact surface 16 of the test element 6, the contact element 4 and the contact 20 which, for example, is connected to the electrical cables 22 of an electrochemical evaluation circuit (not illustrated) in the evaluation appliance 55.

FIG. 5 shows a fourth embodiment of an electrical connection system in an analysis system according to the invention, for electrical connection of a test element 6 to an evaluation appliance 55.

A slide 2 is arranged in a housing 1 and can be moved between an initial position (FIG. 5, top) and an end position (FIG. 5, bottom) between two stops 13, 15. The slide 2 contains a test element 6 in a holding space 5, which has an inlet opening 7 and a stop 8. A contact element 4 is fixedly connected to the slide 2, and is set at a distance from the contact surface 16 of the test element 6 in the initial position. During movement of the slide 2 to the end position (FIG. 5, bottom), the contact element 4 slides along a contact-pressure element 12, which is connected to the housing 1. As a result, the contact element 4 is resiliently deformed such that its first end 21 is moved towards the contact surface 16 of the test element 6, and is pressed against the contact surface 16 in the end position by means of the contact-pressure element 12, which is provided as the means 24 for moving the contact element, so that an electrical contact is produced. When the slide 2 is in the end position, one end 19 of the contact element 4, which projects beyond the slide 2, rests on an electrical contact 20. The electrical contact then exists between the contact surface 16 of the test element 6, the contact element 4 and the contact 20 which, for example, is connected to electrical cables 22 of an electrochemical evaluation circuit (not illustrated) in the evaluation appliance 55.

FIG. 6A shows a fifth embodiment of an analysis system 50 according to the invention.

The test element holder 23 in the analysis system is located under an electrical contact element 4, which is in the form of a toggle lever 25 and is used to make electrical contact with at least one electrical contact surface of an analytical test element 6, and in order to produce an electrical connection to an evaluation appliance (not shown in FIG. 6A) which is included in the analysis system. The contact element 4 is arranged such that it can move relative to the test element holder 23. The contact element 4 can be moved by a rotary movement about a rotation axis 26 towards the contact surface of a test element which is arranged in the measurement position in the test element holder 23.

The test element holder 23 is arranged such that it is fixed relative to the housing 1, and is fixed to it by means of screws 27. A rod 29, which can be moved substantially in the longitudinal direction 28 with respect to the housing 1 and with respect to the test element holder 23, is provided as the means 24 for moving the electrical contact element 4 and its rod end 30 can operate the toggle lever 25 in order to move the contact element 4 onto the contact surface of a test element which is arranged in the measurement position. The toggle lever 25 is held by a spring element 31 in the illustrated initial position, in which it is at a distance from the test element holder 23, for as long as it is not moved by the rod end 30 against the spring force of the spring element 31 towards the test element holder 23.

In the analysis system according to the invention as illustrated in FIG. 6A, the means 24 for movement of the electrical contact element 4 is moved automatically by a drive (not illustrated). The drive comprises an electric motor, which drives a test element removal device 32 for automatic removal of a test element from a test element magazine 33. The test element magazine 33 comprises a container in the form of a drum, which can hold a large number of test elements in individually sealed chambers 34. The test element removal device 32 contains a plunger 35. This plunger 35 is coupled to a threaded rod 37 via a transmission element 36. The threaded rod 37 is rotated by the drive (not illustrated) during operation of the test element removal device 32. The transmission element 36 converts this rotary movement of the threaded rod 37 to a linear movement in the longitudinal direction 28. In consequence, the plunger 35 is likewise moved in the longitudinal direction 28. In order to remove a test element from the test element magazine 33, it is rotated to a position in which the chamber 34 which contains the test element to be removed is arranged in front of the test element holder 23. The plunger 35 is then moved linearly in the longitudinal direction 28, breaks through the seal on the chamber 34, and pushes the test element out of the chamber 34 into the test element holder 23.

The rod 29 is likewise moved in the longitudinal direction parallel to the plunger 35, since it is also coupled to the threaded rod 37, via the transmission element 36. As soon as the plunger 35 has pushed the test element that has been removed from the test element magazine 33 and is in the test element holder 23 into the measurement position, the rod end 30 reaches the toggle lever 25 and tilts this towards the test element, so that the contact element 4 makes contact with the contact surface of the test element. In this position, the contact element 4 produces an electrical connection between the test element and the evaluation appliance (not illustrated in FIGS. 6A-B), thus allowing an electrochemical analysis to be carried out on a sample on the test element.

Figure 6B:
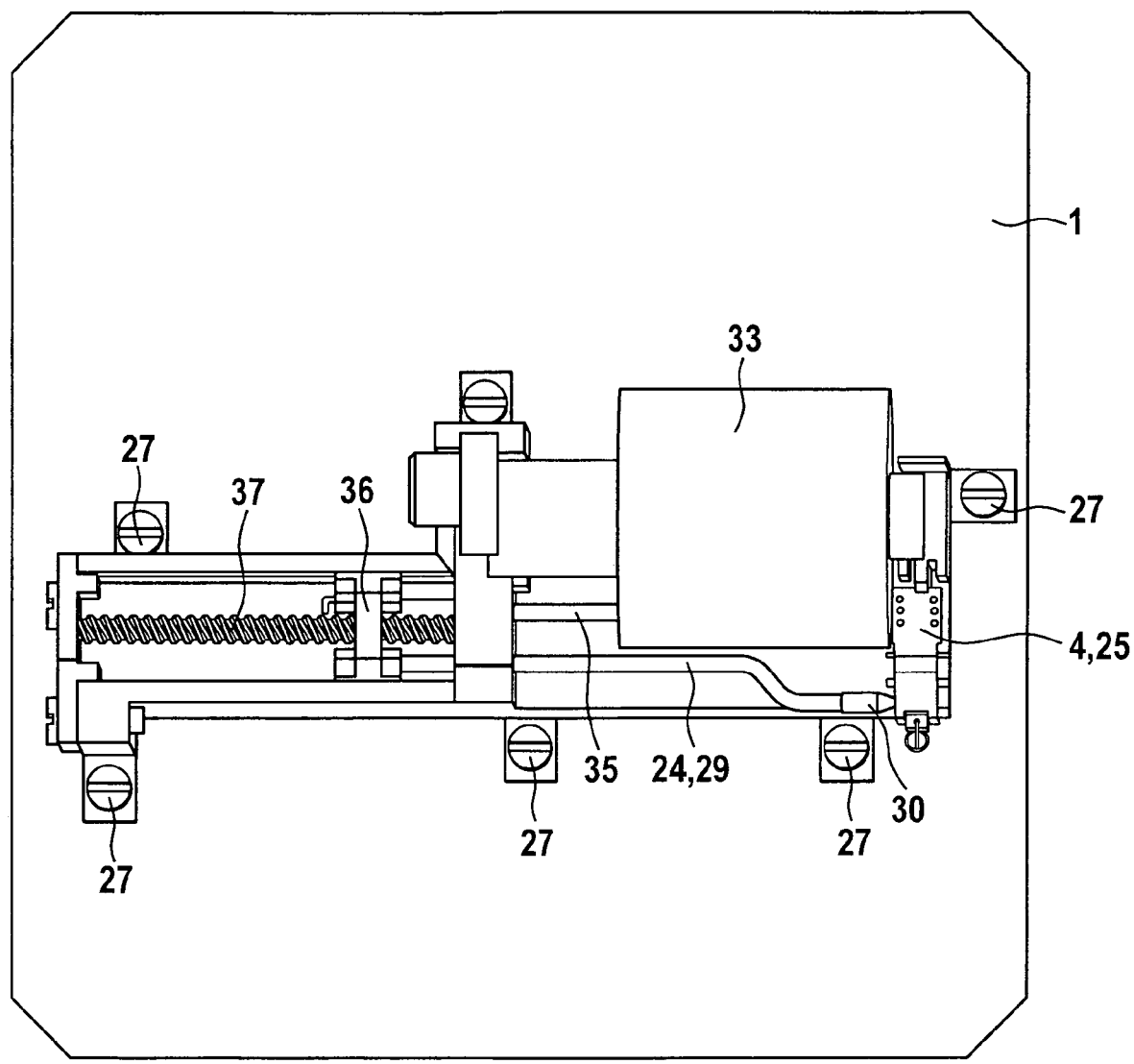
FIG. 6B shows a plan view of the analysis system shown in FIG. 6A.

FIG. 6B shows a plan view of the analysis system shown in FIG. 6A.

This plan view illustrates, in particular, the electrical contact element 4 (toggle lever 25), the means 24 for moving the contact element 4 (rod 29 with the rod end 30), the threaded rod 37, the transmission element 36, the plunger 35, the test element magazine 33, the housing 1 and the screws 27.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention may be identified herein as preferred or particularly advantageous, it is contemplated that the present invention is not necessarily limed to these preferred aspects of the invention.

What is claimed is:

1. An analysis system for analysis of a liquid sample on an analytical test element, comprising:
    an evaluation appliance for evaluation of electrical signals, and an electrical connection system,
    the electrical connection system comprising:
        a housing containing a test element holder and at least one electrical contact element,
            the test element holder being movable relative to the housing and configured to hold and position an analytical test element in one of an initial position and an end position within the analysis system,
            each said electrical contact element being at least partially attached to the test element holder and configured to make electrical contact with at least one electrical contact surface of an analytical test element provided in the test element holder in order to produce an electrical connection between the contact surface and the evaluation appliance,
            the test element holder comprising a slide that is moveable between the initial position and the end position within the housing, the end position comprising a measurement position,
            the slide defining a holding space bounded by a stop and configured to receive a test element through an inlet opening in the slide, each said contact element being mounted on the slide and recessed relative to the test element in a depression in the holding space when the slide is in the initial position,
            the attachment of the contact element to the test element holder being such that the contact element is movable relative to the test element holder and relative to the position of the test element holder between and including the initial position and the end position, the contact element being set at a distance from the contact surface of the test element when the test element is held in the holding space and the slide is in the initial position,
        wherein the analysis system has a means engaged by movement of the test element holder relative to the housing for moving the electrical contact element into contact with the contact surface when the test element is positioned in the measurement position in the test element holder, in order to produce an electrical connection between the contact surface and the evaluation appliance.

2. The analysis system of claim 1, the contact element extending through and being moveably maintained within an opening in the slide, the means for moving the contact element comprising a contact-pressure element fixedly mounted within the housing and outside the slide.

3. The analysis system of claim 2, the contact-pressure element having a guide surface configured to displace the contact element into the holding space toward the contact surface as the slide is moved from the initial position to the end position.

4. The analysis system of claim 3, the contact-pressure element comprising an inclined plane configured to guide the contact element as the slide is moved from the initial position to the end position.

5. The analysis system of claim 2, the contact-pressure element comprising an electrically conductive material and being in electrical communication with the evaluation appliance.

* * * * *